US010928369B2

United States Patent
Herrier et al.

(10) Patent No.: US 10,928,369 B2
(45) Date of Patent: Feb. 23, 2021

(54) METHOD OF CALIBRATING AN ELECTRONIC NOSE

(71) Applicants: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR); UNIVERSITE GRENOBLE ALPES, Saint-Martin-d'Heres (FR); ARYBALLE TECHNOLOGIES, Grenoble (FR)

(72) Inventors: Cyril Herrier, Grenoble (FR); Yanxia Hou-Broutin, Bilieu (FR); Francois-Xavier Gallat, Grenoble (FR); Thierry Livache, Jarrie (FR); Tristan Rousselle, Grenoble (FR)

(73) Assignees: ARYBALLE TECHNOLOGIES, Grenoble (FR); CENTRE NATIONAL DE LA RECHERCHE SCIENTIFIQUE, Paris (FR); COMMISSARIAT A L'ENERGIE ATOMIQUE, Paris (FR); UNIVERSITE GRENOBLE ALPES, Saint-Martin-D'Heres (FR)

( * ) Notice: Subject to any disclaimer, the term of this patent is extended or adjusted under 35 U.S.C. 154(b) by 0 days.

(21) Appl. No.: 16/490,527

(22) PCT Filed: Mar. 2, 2018

(86) PCT No.: PCT/EP2018/055233
§ 371 (c)(1),
(2) Date: Nov. 15, 2019

(87) PCT Pub. No.: WO2018/158458
PCT Pub. Date: Sep. 7, 2018

(65) Prior Publication Data
US 2020/0088702 A1   Mar. 19, 2020

(30) Foreign Application Priority Data
Mar. 3, 2017  (FR) ..................... 1751751

(51) Int. Cl.
*G01N 33/00* (2006.01)
*G01N 21/41* (2006.01)
(Continued)

(52) U.S. Cl.
CPC ..... *G01N 33/0006* (2013.01); *G01N 21/4133* (2013.01); *G01N 21/553* (2013.01); *G01N 21/61* (2013.01)

(58) Field of Classification Search
CPC ........... G01N 33/6854; G01N 2800/52; G01N 33/6896; G01N 2333/575;
(Continued)

(56) References Cited

U.S. PATENT DOCUMENTS

| 6,672,129 B1* | 1/2004 | Frederickson | A61M 15/02 347/20 |
| 7,610,142 B1* | 10/2009 | Hoard | F01N 13/008 60/274 |
| 9,709,491 B1* | 7/2017 | Murphy | G01J 3/0297 |

(Continued)

FOREIGN PATENT DOCUMENTS

| WO | WO2007/003674 | 1/2007 |
| WO | WO2015/0102090 | 7/2015 |
| WO | WO2015102090 | 7/2015 |

OTHER PUBLICATIONS

Vargas-Sansalvador, et al.,"Compact Optical Instrument for Simultaneous Determination of Oxygen . . . ," Michrochimica Acta, vol. 172, No. 3-4, Dec. 2010.
(Continued)

*Primary Examiner* — Michael P Stafira
(74) *Attorney, Agent, or Firm* — Steven M. Greenberg, Esq.; Shutts & Bowen LLP (57) ABSTRACT

The invention relates to a method for calibrating an electronic nose, said electronic nose comprising a plurality of optical sensors arranged on a surface and capable of being in contact with a gaseous medium of interest, said optical sensors being capable of delivering a signal representative of the local optical index of the gaseous medium of interest (Continued)

when they are excited by photons, the method being characterized in that it comprises the following steps: after having placed the electronic nose in a gaseous medium of interest at the initial pressure ($P_0$) and the initial temperature ($T_0$): a) sending photons in the direction of the sensors so as to excite said sensors; b) measuring the signal delivered by each of the sensors, this measurement providing as many responses as there are sensors; c) modifying the pressure and/or temperature of the gaseous medium of interest; d) repeating step b); and e) for each sensor, determining a correction factor such as a variation in the signal between steps d) and b) corrected by the correction factor either equal to or substantially equal to a variation in the signal between these same steps for a reference, said reference being provided by a reference sensor or a combination of reference sensors. Such a method allows a physical calibration, that in the present case is relative, to be performed between the different sensors.

15 Claims, 4 Drawing Sheets

(51) Int. Cl.
    *G01N 21/552*    (2014.01)
    *G01N 21/61*    (2006.01)

(58) Field of Classification Search
CPC ..... G01N 2800/2821; G01N 33/54346; G01N 33/553; G01N 33/558; G01N 33/56983; G01N 33/573; G01N 33/6893; G01N 1/38; G01N 21/554; G01N 21/648; G01N 2333/4709; G01N 2333/9015; G01N 2469/10; G01N 2469/20; G01N 2500/02; G01N 2500/04; G01N 2800/50; G01N 33/53; G01N 33/54373; G01N 33/56911; G01N 33/574; G01N 33/57423; G01N 33/57434; G01N 33/57484; G01N 33/58; G01N 33/74; G01N 15/1459; G01N 2015/0065; G01N 2015/1006; G01N 2021/775; G01N 21/25; G01N 21/41; G01N 21/6458; G01N 21/67; G01N 21/718; G01N 21/77; G01N 2201/088; G01N 2333/015; G01N 2333/02; G01N 2333/181; G01N 2333/185; G01N 2333/186; G01N 2333/35; G01N 2333/47; G01N 2333/4724; G01N 2333/495; G01N 2333/51; G01N 2333/54; G01N 2333/5757; G01N 2333/70535; G01N 2405/00; G01N 2440/14; G01N 2458/40; G01N 2469/00; G01N 2500/10; G01N 27/127; G01N 27/416; G01N 27/447; G01N 27/44791; G01N 27/453; G01N 2800/10; G01N 2800/102; G01N 2800/12; G01N 2800/122; G01N 2800/222; G01N 2800/226; G01N 2800/28; G01N 2800/2828; G01N 2800/32; G01N 2800/324; G01N 2800/347; G01N 2800/56; G01N 2800/60; G01N 33/4915; G01N 33/50; G01N 33/5011; G01N 33/5073; G01N 33/5088; G01N 33/5302; G01N 33/531; G01N 33/532; G01N 33/534; G01N 33/543; G01N 33/5432; G01N 33/54326; G01N 33/54366; G01N 33/5438; G01N 33/54386; G01N 33/569; G01N 33/56927; G01N 33/56938; G01N 33/5695; G01N 33/56966; G01N 33/56988; G01N 33/57407; G01N 33/57415; G01N 33/5764; G01N 33/5767; G01N 33/577; G01N 33/582; G01N 33/68; G01N 33/6845; G01N 33/6863; G01N 33/6869; G01N 33/6872; G01N 33/86; G01N 33/94; G01N 35/0098; G01N 33/497; G01N 2033/4975; G01N 1/24; G01N 2030/025; G01N 33/0001; G01N 33/006; G01N 33/0031; G01N 33/0047; G01N 1/22; G01N 1/40; G01N 2021/7793; G01N 21/01; G01N 21/31; G01N 21/553; G01N 27/026; G01N 27/126; G01N 27/3275; G01N 27/4146; G01N 29/022; G01N 29/036; G01N 33/0036; G01N 33/0098; G01N 33/54306; G01N 1/14; G01N 1/2214; G01N 1/2247; G01N 1/2273; G01N 1/30; G01N 1/31; G01N 1/405; G01N 2001/2229; G01N 2001/2244; G01N 2001/245; G01N 2001/302; G01N 2021/0346; G01N 2021/0367; G01N 2021/0378; G01N 2021/0389; G01N 2021/052; G01N 2021/1776; G01N 2021/391; G01N 2021/398; G01N 2021/7789; G01N 2027/222; G01N 2030/0095; G01N 2030/628; G01N 2030/743; G01N 2030/8813; G01N 2030/884; G01N 2033/0068; G01N 2033/4977; G01N 21/03; G01N 21/0303; G01N 21/05; G01N 21/17; G01N 21/272; G01N 21/274; G01N 21/33; G01N 21/3504; G01N 21/39; G01N 21/4133; G01N 21/49; G01N 21/552; G01N 21/61; G01N 21/62; G01N 21/6428; G01N 21/645; G01N 21/76; G01N 21/763; G01N 21/7703; G01N 21/78; G01N 21/783; G01N 2291/014; G01N 2291/015; G01N 2291/021; G01N 2291/0256; G01N 2291/0257; G01N 2291/0426; G01N 2333/21; G01N 2333/31; G01N 2333/38; G01N 2333/445; G01N 2333/726; G01N 2333/90241; G01N 27/04; G01N 27/12; G01N 27/122; G01N 27/124; G01N 27/125; G01N 27/128; G01N 27/221; G01N 27/227; G01N 27/3277; G01N 27/3278; G01N 27/4145; G01N 2800/18; G01N 2800/26; G01N 29/032; G01N 29/226; G01N 29/30; G01N 29/32; G01N 29/326; G01N 30/02; G01N 30/461; G01N 30/466; G01N 30/54; G01N 30/7206; G01N 30/722; G01N 30/74; G01N 30/78; G01N 31/12; G01N 33/00; G01N 33/009; G01N 33/0034; G01N 33/004; G01N 33/0042; G01N 33/0062; G01N 33/007; G01N 33/0073; G01N 33/0075; G01N 33/025; G01N 33/2823; G01N 33/2894; G01N 33/48; G01N 33/483; G01N 33/4833; G01N 33/4972; G01N 33/5005; G01N 33/5038; G01N 33/52; G01N 33/5308; G01N 33/542; G01N 33/54313; G01N 33/54393; G01N 33/56905; G01N 33/57411; G01N 33/57442; G01N 33/57449; G01N 33/581; G01N 35/00; G01N 5/02; G01B
11/25; G02B 1/005; G02B 21/0008;
G02B 21/0036; G02B 21/02; G02B
27/58; G02B 3/0037; G02B 5/208; G02B
6/04; G02B 6/10; G01J 1/0411; G01J
1/0422; G01J 1/4228; G01J 2003/423;
G01J 2005/0048; G01J 2005/0077; G01J
3/0205; G01J 3/10; G01J 3/42; G01J
5/04; G01J 5/0812; G01J 5/0825; G01J
5/0831; G01J 5/20; G01J 5/522

See application file for complete search history.

(56) References Cited

U.S. PATENT DOCUMENTS

| | | | | |
|---|---|---|---|---|
| 2012/0019834 | A1* | 1/2012 | Bornhop | G01N 21/45 356/517 |
| 2013/0301052 | A1* | 11/2013 | MacGregor | G01N 21/3504 356/437 |
| 2017/0052133 | A1* | 2/2017 | Opdahl | G01N 21/648 |
| 2018/0263489 | A1* | 9/2018 | Gavaris | A61B 3/145 |
| 2018/0321150 | A1* | 11/2018 | Gavaris | A61B 5/1455 |

OTHER PUBLICATIONS

Palma, et al., "Microcontroller-Bases Portable Instrument for Stabilized Optical Oxgen Sensor," Sensors and Actuators B: Chemical, vol. 121, No. 2, Feb. 2007.

Xiutao Lou, et al., Temperature-Corrected Oxygen Detection Based on Multi-Mode Diode Laser Correlation Spectroscopy, Journal of Spectroscopy, vol. 32, No. 30, Jan. 2013.

\* cited by examiner

METHOD OF CALIBRATING AN ELECTRONIC NOSE

CROSS-REFERENCE TO RELATED APPLICATIONS

This application is a § 371 national phase entry of International Application No. PCT/EP2018/055233, filed Mar. 2, 2018, which claims priority to French Patent Application No. 1751751, filed Mar. 3, 2017.

The invention concerns a method for calibrating an electronic nose.

An electronic nose generally consists of several sensors, designed to recognize the presence of a target compound, such as a chemical or biological analyte, in a gas sample.

Sensors are generally not specific to a particular target compound. Also, in a given application, a comparison is usually made between the data provided by the different sensors of the electronic nose, which provide a recognition imprint, and reference data, for example resulting from a prior learning for the target compound in question.

One technique known to obtain, in use, a recognition imprint is surface plasmon resonance imaging (better known by the acronym SPR for "Surface Plasmon Resonance"). This technique detects a local change in optical index (optical index=refractive index) that characterizes the interaction of the target compound with each sensor of the electronic nose.

However, since the chemical affinities of each electronic nose sensor with a given target compound are not known at first glance and only the imprint of all sensors is taken into account for the recognition of the target compound, it is necessary for each sensor to respond reproducibly with respect to each other and from one experiment to another. Similarly, it is necessary that different electronic noses, in particular from different manufacturing batches, can give reproducible answers.

These same difficulties with reproducibility are encountered with sensors designed to be specific to a particular target compound.

Otherwise, it is not possible to obtain a reliable recognition imprint that can be compared with the reference data.

Indeed, although every care is taken in the manufacture of an electronic nose, the sensors differ slightly from their ideal design.

There are already several techniques available for calibrating an electronic nose.

A first technique is proposed in the Permapure documentation of Jun. 14, 2016, entitled "Gas Sensor Calibration" accessible on the website http://www.permapure.com/wp-content/uploads/2013/01/calibration.pdf, taken from the book "Air Monitoring for Toxic exposure", Henry J. McDermott, $2^{nd}$ edition, 2004, John Wiley & Sons Inc. pp. 161-173 (D1).

In this technique, calibration is performed by injecting a gas containing an organic reference compound.

A second technique consists in using a prediction model after injection of an organic reference compound at different concentrations. This is what is proposed by Tian & al, "*On-line calibration of semiconductor gas sensors based on, prediction model*", J. of computers, vol. 8, p. 2204, September 2013 (D2).

For these two techniques, the stimulus common to all sensors is therefore based on a reference organic compound. We are talking about chemical calibration.

In addition, and in practice, if you want to obtain a versatile electronic nose, several organic reference compounds are then expected.

However, with these techniques, depending on the concentration of the reference organic compound, or by switching from one reference organic compound to another, there may be distinct affinities between the different sensors of the electronic nose.

This is then detrimental to the quality of the calibration.

Moreover, this type of calibration is not very practical since it is sometimes necessary to have the various organic reference compounds with you.

One of the objectives of the invention is thus to propose a method for calibrating an electronic nose that does not have at least one of the above-mentioned disadvantages.

To achieve this objective, the invention proposes a method for calibrating an electronic nose, said electronic nose comprising a plurality of optical sensors arranged on a surface and capable of being in contact with a gaseous medium of interest, said optical sensors being capable of delivering a signal representative of the local optical index of the gaseous medium of interest when they are excited by photons, the method being characterized in that it comprises the following steps, after having placed the electronic nose in a gaseous medium of interest at the initial pressure $P_0$ and the initial temperature $T_0$:

a) emitting photons in the direction of the sensors so as to excite said sensors;

b) measuring the signal delivered by each of the sensors, this measurement providing as many responses as there are sensors;

c) modifying the pressure and/or temperature of the gaseous medium of interest;

d) repeating step b); and e) for each sensor, determining a correction factor such that a variation in the signal between steps d) and b) corrected by the correction factor is equal or substantially equal to a variation in the signal between these same steps for a reference, said reference being provided by a reference sensor or a combination of reference sensors.

It should be recalled that sensors, given their sensitivity to a change in local optical index due to the reading methods used, are intrinsically sensitive to temperature and/or pressure. This is considered by the person skilled in the art as a disadvantage.

In the context of the invention, it is therefore understood that it is proposed to use this sensitivity to perform a physical calibration.

The method according to the invention may include at least one of the following characteristics, taken alone or in combination:

prior to step a), the pressure $P_0$ and/or temperature $T_0$ of the gaseous medium of interest is determined;

the measurement performed in step b) or d), for example a reflectivity or transmittivity measurement, is carried out over a period of between 0.1 s and 60 mn, preferably between 1 s and 10 mn, then averaged;

before implementing step e), steps c) and d) are repeated N times, with N being a natural integer greater than or equal to 1, so that the pressure and/or temperature of the gaseous medium of interest is different from a pressure and/or temperature of the gaseous medium of interest for which a measurement has already been made;

in step c), the pressure and/or temperature of the gaseous medium of interest is modified to another known value;

in step c), the pressure of the gaseous medium of interest is modified by a value between +10 mbar and +2 bar, preferably between +50 mbar and +150 mbar or between −10 mbar and −900 mbar, preferably between −50 mbar and −150 mbar; and/or the temperature of the gaseous medium is modified by a value between +1° C. and +100° C., preferably between +5° C. and +15° C. or between −1° C. and −50° C., preferably between −5° C. and −15° C.;

just before step e), an additional step is implemented consisting in modifying the pressure and/or temperature of the gaseous medium of interest to the initial pressure ($P_0$) and/or the initial temperature ($T_0$);

the optical sensor is selected from a plasmon effect sensor, for example on a flat surface, optical fiber or nanocavities, or a sensor capable of operating by refractometry, for example a resonator sensor.

To achieve this same objective, the invention also proposes a method for calibrating an electronic nose, said electronic nose comprising a plurality of optical sensors arranged on a surface and capable of being in contact with a gaseous medium of interest, said optical sensors being capable of delivering a signal representative of the local optical index of the gaseous medium of interest when excited by photons, the method being characterized in that it comprises the following steps, after having placed the electronic nose in a gaseous medium of interest at the initial pressure $P_0$ and the initial temperature $T_0$:

A) determining the initial pressure $P_0$ and the initial temperature $T_0$ of the gaseous medium of interest;

B) emitting photons in the direction of the optical sensors so as to excite said sensors;

C) measuring the signal delivered by each of the optical sensors, this measurement providing as many responses as there are optical sensors;

D) modifying the pressure and/or temperature of the gaseous medium of interest to another or other known values;

E) repeating step C); and

F) for each sensor, calculating the evolution of the optical index of the gaseous medium of interest using the measurements made in steps C) and E).

This method, according to the invention, may include at least one of the following characteristics, taken alone or in combination:

prior to step A), the pressure and/or temperature of the gaseous medium of interest is adjusted to a predetermined value;

the measurement performed in step C) or E), for example a reflectivity or transmittivity measurement, is carried out over a period of between 0.1 s and 60 mn, preferably between 1 s and 10 mn, then averaged;

before implementing step F), steps D) and E) are repeated N times, with N being a natural integer greater than or equal to 1, so that the pressure or, as appropriate, the temperature of the gaseous medium of interest is different from a pressure or, as appropriate, a temperature of the gaseous medium of interest for which a measurement has already been made;

in step D) the pressure of the gaseous medium is modified by a value between +10 mbar and +2 bar, preferably between +50 mbar and +150 mbar or between −10 mbar and −900 mbar, preferably between −50 mbar and −150 mbar; and/or the temperature of the gaseous medium is modified by a value between +1° C. and +100° C., preferably between +5° C. and +15° C., or between −1° C. and −50° C., preferably between −5° C. and −15° C.;

just before step F), an additional step is implemented consisting in modifying the pressure and/or temperature of the gaseous medium of interest to the initial pressure ($P_0$) and/or initial temperature ($T_0$);

the optical sensor is selected from a plasmon effect sensor, for example on a flat surface, optical fiber or nanocavities, or a sensor capable of operating by refractometry, for example a resonator sensor.

Figure 1:
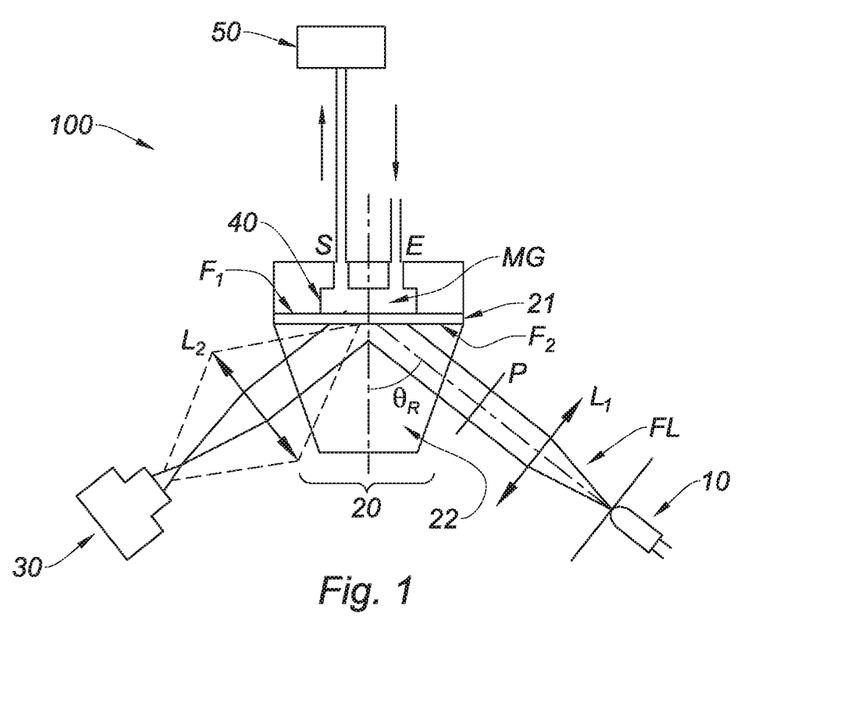
FIG. 1 represents a possible installation for implementing a method in conformity with the invention, based on a reflectivity measurement and a pressure evolution of the gaseous medium associated with the electronic nose.

Other characteristics, purposes and advantages of the invention will emerge from the description made with reference to the annexed figures given by way of example, and in which:

FIG. 4, which includes FIGS. 4(a) to 4(c), represents an application case that can be performed with the installation of FIGS. 1 and 2, with a gaseous medium containing air (dry) and ethanol as an analyte;

FIG. 1 shows an example of an experimental installation 100 for implementing the method for calibrating an electronic nose according to the invention.

This experimental installation 100 includes a light source 10, for example a LED, capable of emitting a given wavelength, an electronic nose 20 and an optical probe 30, for example a CCD camera. A lens L1 and a polarizer P can be provided between the light source 10 and the electronic nose 20. A lens L2 can also be provided between the electronic nose 20 and the optical probe 30.

It should be noted that the optical probe 30 is arranged on the same side of the metal layer 21 as the light source 20. This experimental installation 100, therefore, allows reflection measurements to be made.

The electronic nose 20 includes a metallic layer 21, in this case in Gold (Au), flat.

The electronic nose 20 also includes a plurality of sensors $C_1, \ldots, C_N$ arranged on a first face F1 of said metal layer 21 so that said first face F1 of the metal layer 21 and said sensors are in contact with a gaseous medium, by nature dielectric. As with any electronic nose, there are at least two optical sensors of different chemical sensitivity among the many optical sensors of the electronic nose.

The electronic nose 20 also includes a support 22 for said metal layer 21. The support 22 is arranged against a second face F2 of the metal layer 21, said second face F2 being opposite to said first face F1. In general, the support 22 is chosen from a dielectric material, transparent at the wavelength that the light source 10 is intended to emit and having an optical index $n_s$ higher than the optical index $n_G$ of the gaseous medium (optical index=refraction index). In this case, it is a prism, made of glass. Another thin metal layer (not shown), for example made of Chrome (Cr), is provided between the second face F2 of the metal layer 21 and the support 22 to ensure the adhesion of the metal layer 21 on the support 22.

Such an installation 100 allows to generate a plasmon resonance on the first face of the metal layer 21 which is in contact with the gaseous medium. More precisely, if we define the angle of incidence between the direction of propagation of the light beam FL and the normal to the metal layer 21, we can define the following relationship:

$$n_S \sin(\theta_R) = \sqrt{\frac{\varepsilon_m \varepsilon_g}{\varepsilon_m + \varepsilon_g}} \quad (R1)$$

where:
$n_s$ is the refraction index of the support 22,
$\varepsilon_m$ is the permittivity of the metal forming the metal layer 21,
$\varepsilon_g$ is the permittivity of the gaseous medium MG, and
$\theta_R$ is the angle of incidence of plasmon resonance.

The relationship (R1) implicitly involves the wavelength of the light beam FL emitted by the optical source 10. In fact, and for example, the optical index $n_G$ of the gaseous medium MG and therefore its permittivity $\varepsilon_g$ depend on the wavelength.

Thus, for a given wavelength of the light beam FL, for a given metal layer 21 (nature of the metal material) and for a given gaseous medium MG, there is an angle of incidence $\theta_R$ as defined above, which makes it possible to obtain the plasmon resonance.

This experimental installation 100 therefore takes over the characteristics of Kretschmann's configuration.

The manufacture of such a Kretschmann's configuration is known to the person skilled in the art and is therefore not specified. However, reference may be made to the article by Guedon & al. entitled *"Characterization and Optimization of a Real-Time, Parallel, Label-Free, Polypyrolle based DNA Sensor by Surface Plasmon Imaging"*. Anal. Chem., 2000, vol. 72, pp. 6003-6009 for more information.

Plasmon resonance allows in this case to induce a plasmon wave at the interface between the metal layer and the gaseous medium, the amplitude of which allows to observe with good sensitivity local variations of optical properties, such as a variation of optical index or a variation of reflectivity. Also, in the case of plasmon resonance, the signal delivered by the sensors $C_1, \ldots, C_N$ may in particular be representative of a variation in reflectivity.

The applicant was able to see that it was possible, with the experimental installation 100, to carry out a calibration, in this case relative, of the sensors, by varying the pressure and/or temperature of the gaseous medium MG.

By relative calibration, we mean a calibration of the sensors with respect to each other, and more precisely by choosing a sensor as a reference or a combination of sensors as a reference, the other sensors being then calibrated with respect to this reference sensor or combination of sensors as a reference. It is therefore understood that the reference sensor is a sensor chosen among the different optical sensors of the electronic nose or that, similarly, the combination of reference sensors is a set of sensors chosen among the different optical sensors of the electronic nose. In this relative calibration, there is always a common stimulus, as this is necessary to ensure an identical response from all sensors. This common stimulus is the pressure and/or temperature of the gaseous medium MG. However, exact knowledge (value) of the common stimulus is not necessary to perform a relative calibration.

On the other hand, this relative calibration does not allow the electronic nose to be calibrated to ensure that when in use (i.e. after calibration and to detect, for example, the presence of a particular target compound), the use of a device of the Kretschmann's configuration type will provide absolute values of a local optical index variation allowing to characterize that particular target compound.

However, a chemical calibration can be carried out beforehand, for example in the factory. This chemical calibration can be carried out using a known technique, such as that described in document D1 or D2.

In this case, the relative calibration performed as part of the invention will certainly allow the electronic nose to be calibrated so that it can be used.

The experimental installation 100 was more precisely designed to ensure a common pressure stimulus. For this purpose, the metal layer 21 and its sensors are housed in a chamber 40 with an input E and an output S. The output S is connected to a pump 50 to supply the chamber with a perfectly controlled gas flow. This means that the gas flow rate is controlled, i.e. known, to obtain a laminar gas flow in the chamber. There is indeed a link between the pressure and the velocity of the gas flow. Typically, we can rely on Bernoulli's relationship in the case of a Newtonian fluid.

A first method according to the invention is a method for calibrating an electronic nose, said electronic nose 20 having a plurality of optical sensors arranged on a surface and capable of being in contact with a gaseous medium of interest, said optical sensors being capable of delivering a signal representative of the local optical index of the gaseous medium of interest when excited by photons, the method being characterized in that it comprises the following steps, after having placed the electronic nose in a gaseous medium of interest at the initial pressure $P_0$ and the initial temperature $T_0$:

(a) emitting photons in the direction of the optical sensors so as to excite the said sensors;

(b) measuring the signal delivered by each of the optical sensors, this measurement providing as many responses as there are optical sensors;

(c) modifying the pressure and/or temperature of the gaseous medium of interest;

(d) repeating step b); and (e) for each sensor, determining a correction factor such that a variation in the signal between steps d) and b) corrected by the correction factor is equal to or substantially equal to a variation in the signal between these same steps for a reference, said reference being provided by a reference optical sensor or a combination of reference optical sensors.

This first calibration method makes it possible to carry out a relative calibration.

Indeed, once the corrective factors for the various sensors are determined, the calibration of the electronic nose is done. It only then remains to take into account before starting an effective measurement with this electronic nose. An example is given below, in which this first method is implemented with the experimental installation 100.

Figure 2:
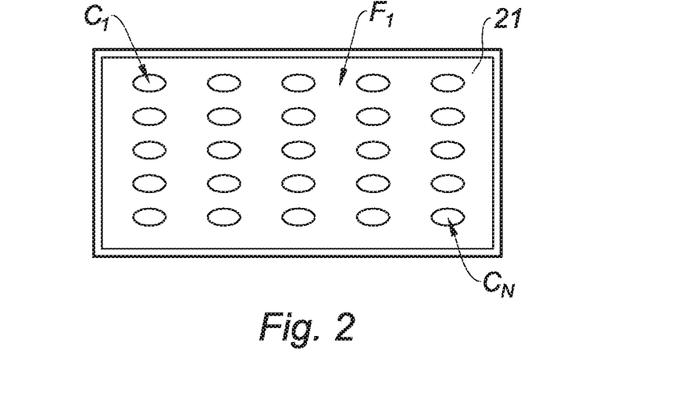
FIG. 2 is a typical image generated by the above-mentioned installation on which the sensors of the electronic nose are visible.

FIG. 2 is a view of the metal layer 21 and its sensors $C_1, \ldots, C_N$.

The metal layer 21, made of Gold, has a complex permittivity $\varepsilon_m$, at a wavelength of 632 nm, which is expressed as $\varepsilon_m = \varepsilon_r + i^* \varepsilon_i = -11.6 + i^* 1.5$ (with $i^2 = -1$).

In addition, all optical sensors are trained by the technique proposed by Hou & al, "*Continuous evolution profiles for electronic-tongue-based analysis*", Angewandte Chem. Int. Ed. 2012, vol. 51, pp. 10394-10398; with decanthiol, for example the optical sensors obtained after surface functionality are then all round in shape.

Measurements can be made for all sensors. Nevertheless, for the sole purpose of demonstration, it has been chosen here to select only four of them. This can be easily done by providing a mask to cover sensors for which no response is desired during calibration.

The gaseous medium MG is dry air.

The pressure and temperature of the dry air in the chamber in which the experiment is carried out is such that the initial pressure is $P_0 = 1,063$ bar and the temperature $T_0$ is such that $T_0 = 25°$ C.

As a reminder, in order to obtain a relative calibration, it is not necessary to know these data $T_0$, $P_0$. This is, however, important for performing a chemical calibration.

In addition, these values allow, by the relationship R1, to calculate the theoretical angle of incidence allowing to obtain the plasmon resonance.

The wavelength $\lambda$ of the light beam FL is such that $\lambda = 632$ nm.

Under these conditions ($T_0$, $P_0$ and $\lambda$), the relative static permittivity $\varepsilon_g/\varepsilon_0$ of the gaseous medium is such that $\varepsilon_g/\varepsilon_0 = 1.00058986$ where $\varepsilon_0$ is the vacuum permittivity.

In addition, and as already indicated, the support 22 is a prism, correctly oriented, made of glass. Its optical index is $n_s = 1.51$.

From these different values, we then deduce that the angle of incidence $\theta_R$ as previously defined which makes it possible to obtain the plasmon resonance, in accordance with the relationship (R1), is $\theta_R = 43°$.

It should be noted that, as an alternative, this angle can be searched experimentally.

The reflectivity response of each of the four selected sensors can then be obtained at pressure $P_0$. The acquisition of the reflectivity variation for each of these sensors is carried out in this case over several minutes in order to obtain, for each sensor, a certain number of values which are then advantageously averaged in order to improve the accuracy of the measurement.

To carry out the following step, a pressure jump, in this case a positive pressure jump of 100 mbar is performed to set the pressure to a value P1=1.163 mbar. At the same time, the temperature in the room has not modified.

In this example, it was chosen to repeat steps b) and c) seven times to define eight pressure levels.

Figure 3:
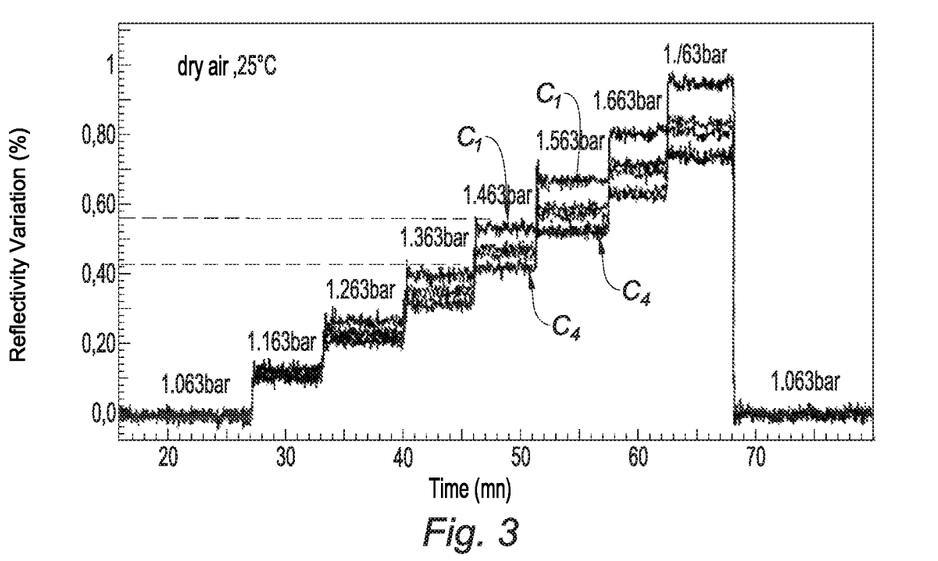
FIG. 3 shows the results of reflectivity measurements performed with the installation of FIGS. 1 and 2, with dry air as the gaseous medium.

The reflectivity measurement results are shown in FIG. 3 (signals from optical sensors $C_1, \ldots, C_N$). This FIG. 3 shows the evolution of the reflectivity variation (%) over time and for each of the four selected sensors. The reflectivity (%) is defined by the ratio of the intensity of the light beam received by the optical probe to the intensity of the light beam sent by the optical source.

To the extent that, several pressure levels of the gaseous medium are implemented over time, it can be observed that the reflectivity that is measured is also in the form of levels.

These results show that it is quite possible, with a plasmon resonance apparatus, to measure the influence of the pressure of the gaseous medium, with the pressure of this gaseous medium as a common stimulus.

These results also show the need for calibration of the various sensors since there is a difference in the reflectivity response of each sensor when the pressure is no longer the reference pressure $P_0$ for which the experimental installation was initially prepared. Indeed, if the sensors provide different reflectivities under identical conditions (temperature and pressure of the gaseous medium, wavelength, in particular to define the permittivity of the gaseous medium) this means that each of the sensors does not see the same plasmon resonance angle (cf. relationship R1), or that they have a variable sensitivity related to, for example, the nature of the compound forming the sensor, in other words that they are offset from each other with respect to the plasmon resonance peak.

Therefore, once the results in FIG. 3 are obtained, step e) is implemented.

For this purpose, in this case, a sensor has been chosen as a reference, for which the reflectivity variation is considered to be correct, for all pressure levels.

For each of the other sensors, and at each pressure level, a correction factor was then determined such that a signal difference between steps d) and b) (difference in reflectivity variation here) is equal or substantially equal to a variation in reflectivity of the reference sensor.

For example, in FIG. 3 at a pressure of 1.463 bar, the reference sensor, C1, indicates a measured reflectivity change of 0.54%, considered correct, and the sensor C4 a measured reflectivity change of 0.42%. For the sensor C4, the correction factor is 54/42 to obtain a corrected reflectivity variation of the sensor C4, equal to the reflectivity variation of the reference sensor, or 0.54%.

If a chemical calibration has been previously performed (e.g. by a known method, especially in a factory), it can then be ensured that the relative calibration performed as previously proposed allows the electronic nose to be calibrated correctly because in this case, it is certain that the reference sensor provides correct values.

In the example provided and leading to FIG. 3, the pressure jump is perfectly determined, which makes it possible to know the modified pressure after the implementation of step d).

It should be noted, however, that in this relative calibration method, it is not important to know the exact pressure jump performed in step c), as the correction is not based on the knowledge of this pressure jump. What is important is that the pressure range is consistent with the working range of the electronic nose.

As part of the invention, it is possible to consider implementing a second calibration method for an electronic nose, which also allows a relative calibration to be performed.

More precisely, it is a method for calibrating an electronic nose, said electronic nose having a plurality of optical sensors arranged on a surface and capable of being in contact with a gaseous medium of interest, said optical sensors being capable of delivering a signal representative of the local optical index of the gaseous medium of interest when excited by photons, the method being characterized in that it comprises the following steps, after having placed the electronic nose in a gaseous medium of interest at the initial pressure $P_0$ and the initial temperature $T_0$:

A) determining the initial pressure $P_0$ and the initial temperature $T_0$ of the gaseous medium of interest;

B) emitting photons in the direction of the optical sensors so as to excite said sensors;

C) measuring the signal delivered by each of the optical sensors, this measurement providing as many responses as there are optical sensors;

D) modifying the pressure and/or temperature of the gaseous medium of interest to another or other known values;

E) repeating step C); and

F) for each sensor, calculating the evolution of the optical index of the gaseous medium of interest using the measurements made in steps C) and E).

The steps B), C), D) and E) of the second method are identical to steps a), b), c) and d) of the first method respectively.

However, in this second method, it is necessary to know the pressure $P_0$ and the temperature $T_0$. This is the subject of step A) which is not necessary in the first method according to the invention.

Consequently, step D) of the second method differs from step c) of the first method, in that the value of the pressure, or temperature, or both pressure and temperature, must be known.

For example, if it is decided to vary only the pressure, as is possible with the experimental device 100 described above, the temperature can be kept constant ($T_0$=temperature of the chamber). Indeed, it is important, for this second method, to determine this value of the pressure variation (in this example) in order to be able to implement step F).

Returning to the concrete example described above, after repeating steps C) and D) seven times, we obtain the curve in FIG. 3 comprising of eight pressure levels.

The step F) can be performed as follows.

It is known that the optical index $n_G$ of a gaseous medium MG depends on the temperature T (in ° C.), the pressure P (in Torr) and the wavelength λ (in μm) according to a relationship of the type:

$$(n_G - 1)_{TP} = (n_G - 1)_\lambda * \frac{P}{720.775} * \left[\frac{1 + P*(0{,}817 - 0{,}0133*T)*10^{-6}}{1 + 0.00366*T}\right] \quad (R2)$$

where:

$(n_G-1)_\lambda$ is a quantity representative of the optical index $n_G$ of the gaseous medium MG, at a temperature of 15° C. and a pressure of 1.013 bar (standard conditions), expressed as:

$$(n_G - 1)_\lambda * 10^{-8} = 8342.54 + \frac{2406147}{130 - \lambda^2} + \frac{15998}{38.9 - \lambda^2} \quad (R3)$$

For small pressure variations, i.e. between 1 bar and a few tens of bars, for example 50 bars, the quadratic pressure term of the relationship R2 contributes only very slightly to the evolution of the quantity $$\left(\frac{\partial(n_G - 1)_{TP}}{\partial P}\right)_{C_i}.$$

For example, for dry air at a temperature of about 25° C. and a pressure variation of 2 bars, the contribution of this quadratic term does not exceed 0.1%. Always for dry air at a temperature of about 25° C. and for a pressure variation of 50 bars, the variation of this quadratic term does not exceed a few percent.

Therefore, with the data in FIG. 3, corresponding to a total pressure variation not exceeding 1 bar, it can be considered that the quantity $$\left(\frac{\partial(n_G - 1)_{TP}}{\partial P}\right)_{C_i}$$

does not depend on pressure. In other words, we can consider that the quantity $(n_G-1)_{TP}$ changes linearly with pressure.

In addition, from FIG. 3, it can also be noted that the reflectivity variation R that is measured changes linearly with pressure since for each sensor and each pressure level, a constant value of this measured reflectivity variation is obtained.

Hence, for each sensor, the quantity $(n_G-1)_{TP}$ evolves linearly according to the reflectivity variation. In other words, for each sensor Ci where i denotes the index of the sensor with 1≤i≤N (N a natural integer), we can construct a relationship of the type:

$$(n_G - 1)_{T_0P,Ci} = \left(\frac{\partial(n_G - 1)_{T_0P}}{\partial P}\right)_{C_i} * \left(\frac{\partial R}{\partial P}\right)_{C_i} * R_{Ci} + (n_G - 1)_{T_0P_0,Ci} \quad (R4)$$

where:

the quantity $$\left(\frac{\partial R}{\partial P}\right)_{C_i}$$

comes from the linear regression performed, for the sensor $C_i$, from the reflectivity measurement R, as a function of pressure P (in the example provided, from the data in FIG. 3), $$\left(\frac{\partial(n_G - 1)_{T_0P}}{\partial P}\right)_{C_i}$$

the quantity intervenes, for the sensor $C_i$, to normalize the measured reflectivity variation, $R_{Ci}$ is, for the sensor $C_i$, the measured reflectivity variation (from the FIG. 3).

In the example provided, the gaseous medium is dry air at T=$T_0$=25° C. and the wavelength λ of the light beam FL is such that λ=632 nm.

It can be deduced from this, thanks to the relationships R2 and R3 and taking into account the linear approximation in the pressure range considered, that the quantity $$\left(\frac{\partial(n_G - 1)_{T_0P}}{\partial P}\right)_{C_i} = 2.64 \cdot 10^{-4}$$

(with the units considered).

Similarly, it is also deduced, by the relationship, that the quantity $(n_G-1)_{T_0P_0,Ci}$=0.000275545 ($T_0$=25° C. and $P_0$=1.063 bar).

We thus obtain a relationship R4 giving, for each sensor Ci, the evolution of the local optical index as a function of the data from FIG. 3, namely $$\left(\frac{\partial R}{\partial P}\right)_{Ci}$$

and $R_{Ci}$.

As this is a calibration, each sensor therefore provides, according to the relationship R4, identical evolutions of this local optical index as a function of the pressure of the gaseous medium.

It is understood that more than a relative calibration, this second method also makes it possible to obtain an absolute calibration of the various sensors, insofar as it makes it possible to obtain the evolution of the optical index in accordance with the relationship R4. Indeed, once the different optical index evolutions for the different sensors are determined, the calibration of the electronic nose is done. All that remains is to take it into account before starting an effective measurement with this electronic nose.

In other words, by using this second calibration method to perform a relative calibration, an absolute calibration is also obtained.

If there are slight differences, related to measurement uncertainties, one of these sensors can then be chosen as a reference and the relationship R4 obtained for this sensor can be applied to all the other sensors.

For this second method, and unlike the first method, it is necessary to know the pressure jump with precision (step D) in order to correctly determine, for each sensor, the evolution of the local optical index (step F)).

The FIG. 4 represents a test performed with the experimental installation 100 in the FIG. 1, under the same conditions as above, with the exception of the number of sensors selected for analysis (N=14 sensors) and the nature of the gaseous medium MG. Indeed, here the gaseous medium is dry air loaded with ethanol, at 200 ppm. Ethanol plays the role of an analyte.

The objective of this test is to show a particular application case, with ethanol as an analyte.

Figure 4A:
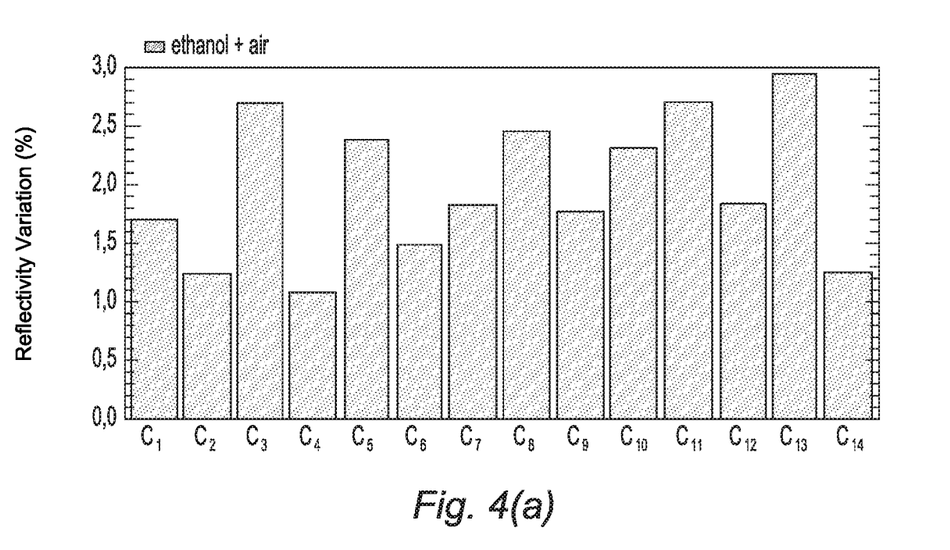
Figure 4B:
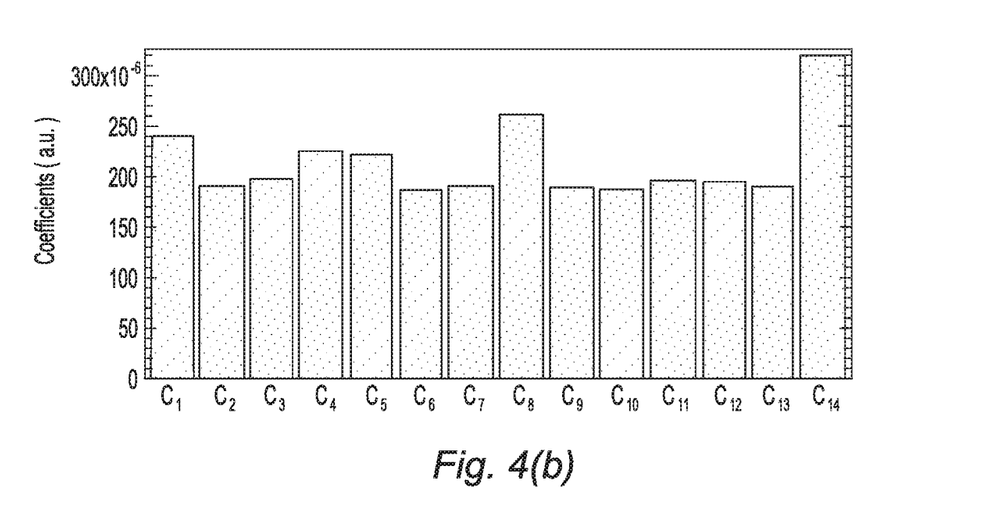
Figure 4C:
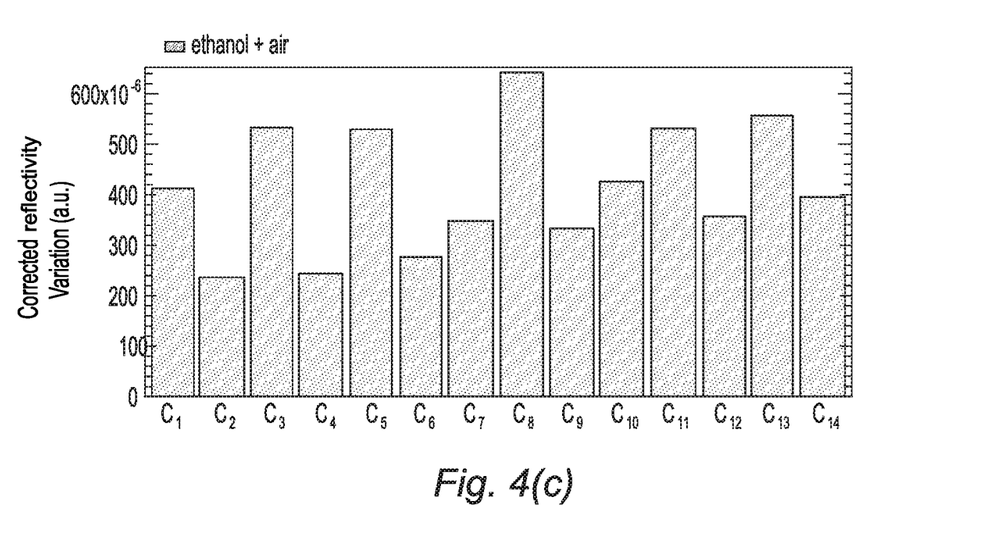

The FIG. 4 includes FIGS. 4(a) to 4(c).

The FIG. 4(a) shows, in the form of a histogram, the measured reflectivity change (raw data—to be compared to the data in FIG. 3).

The corrective factors can then be deduced, for example based on the $C_1$ sensor as a reference.

The FIG. 4(b) shows the corrective factors for each sensor. At this stage, we therefore know the corrective factors leading to the calibration.

Finally, FIG. 4(c) shows the corrected reflectivity variation for each sensor. This FIG. 4(c) therefore corresponds to FIG. 4(a) corrected by FIG. 4(b). At this stage, we are therefore ready to start an effective measurement.

Advantageously, and taking into account the sensitivity of the experimental apparatus 100, it will be possible to modify the pressure of the gaseous medium, at each pressure jump, by a value between +10 mbar and +2 bar, preferably between +50 mbar and +150 mbar or between −10 mbar and −900 mbar, preferably between −50 mbar and −150 mbar.

In addition, to perform accurate measurements, it is advantageous to perform a reflectivity measurement (step b) or d) for the first method or step C) or E) for the second method) over a period of between 0.1 s and 60 mn, preferably between 1 s and 10 mn, then averaged. The duration of the measurement depends on the desired accuracy, but also on the characteristics of the sampling device.

As it was achieved in the example provided, steps c) and d) are advantageously repeated N times before the implementation of step e) or, as the case may be, steps D) and E) are repeated N times before the implementation of step F), with N being a natural integer greater than or equal to 1.

Thus, at each repetition, the pressure of the gaseous medium is different from a pressure (or, as appropriate, the temperature or both the pressure and the temperature) for which a measurement has already been made. This allows more than two measurements to be made and thus increases the quality of the measurements.

In any case, it is advantageous, at the end of the reflectivity measurement and before implementing step e) or as appropriate, step F), to change the pressure back to the initial value $P_0$ (or the temperature T to the value $T_0$ or both the temperature and the pressure) in order to eliminate any drifts of the measurement signals during the measurement. This is what was achieved in the example provided here, where the last measurement was achieved at the pressure $P_0=1.063$ bar (see FIG. 3).

It should be noted that the two methods described above can be implemented in different embodiments.

In particular, and as we will have understood, it is possible to carry out reflectivity measurements (reflectivity variation) based on a change in the temperature T of the gaseous medium MG, either by maintaining the pressure $P_0$ at a constant value the pressure of this gaseous medium or by also varying the pressure of the gaseous medium.

Figure 5:
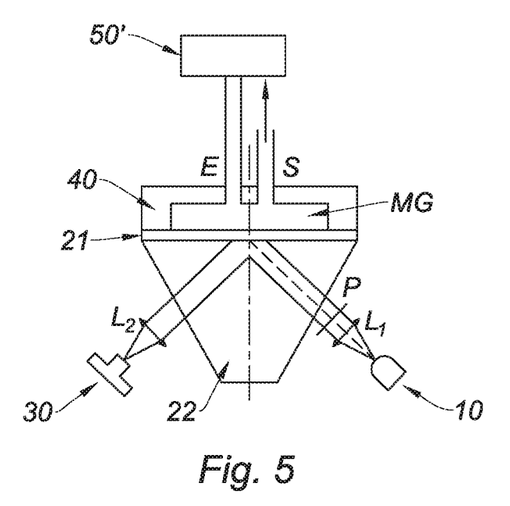
FIG. 5 represents a variant of the installation of FIGS. 1 and 2 to implement a method in accordance with the invention, based on a reflectivity measurement and temperature evolution of the gaseous medium associated with the electronic nose.

This is shown in FIG. 5.

Compared to FIG. 1, it is noted that the experimental installation 100' includes a temperature control device 50', in order to be able to change the temperature. In practice, this device can take the form of an electric wire supplied by the mains to produce a Joule effect heating system with an associated temperature control loop.

To set the ideas, it should be noted that a 10° C. change in the temperature of the gaseous medium MG corresponds substantially to the effect obtained by a pressure change of 100 mbar. We can rely on the relationship R1 for this purpose. Typically, it will therefore be possible to predict, for each measurement, a temperature evolution between +1° C. and +100° C., preferably between +5° C. and +15° C. or between −1° C. and −50° C., preferably between −5° C. and −15° C.

Of course, the above-mentioned control device may be replaced by a temperature and pressure control device when it is desired to vary both temperature and pressure, this device being for example a combination of the means described above to vary temperature on the one hand and pressure on the other.

In addition, whether based (FIG. 1) on a change in the pressure of the gaseous medium (at constant temperature) or (FIG. 5) on a change in the temperature of the gaseous medium (at constant pressure or not), the methods according to the invention can be implemented with a transmittivity measurement, instead of a reflectivity measurement.

Figure 6:
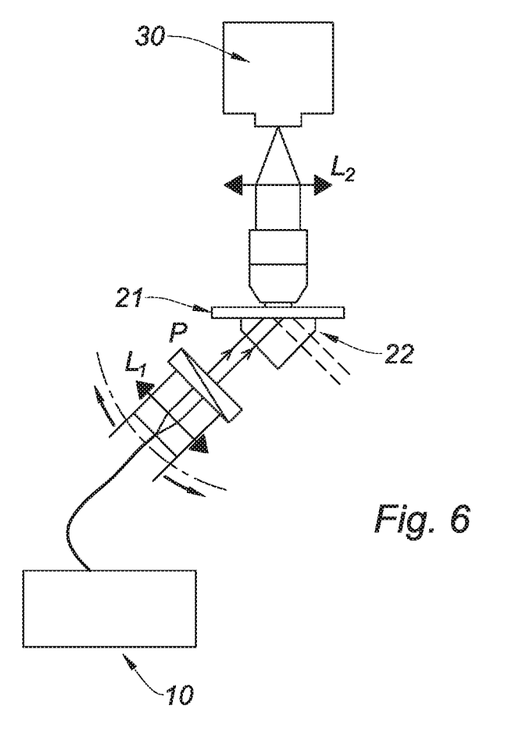
FIG. 6 represents another variant of the installation in FIGS. 1 and 2 to implement a method in accordance with the invention, based on a transmittivity measurement and a pressure and temperature evolution of the gaseous medium associated with the electronic nose.

In FIG. 6, we have thus represented an experimental installation 100" allowing to implement a pressure and/or temperature evolution of the gaseous medium, with a transmittivity measurement. For convenience, however, the pump 50 and/or, as appropriate, the temperature control device 50' have not been shown in this FIG. 6, the objective being simply to represent how the measurement can be performed.

More generally, a method in conformity with the invention may be implemented with an installation different from the installations 100, 100', 100", shown respectively in FIGS. 1, 5 and 6.

Indeed, for all the installations described above, the surface plasmon resonance (SPR) is used in the case of a flat surface (metal layer 21 placed on a flat support 22, in this case a prism).

However, the person skilled in the art knows many other installations that allow measurements based on plasmon resonance to be made.

Some possible techniques that can be used are mentioned below in a non-exhaustive way.

A method in accordance with the invention can be implemented using surface plasmon resonance on optical fiber, whether in reflection or transmission. This technique is for example presented by Burgmeier & al, "*Plasmonic nano-shelled functionalized etch fiber Bragg gratings for highly sensitive refractive index measurements*", Optics Letters, vol. 40(4), pp. 546-549 (2015). The device proposed in this document is used with a liquid medium, but could just as easily be used for a gaseous medium, therefore for an electronic nose.

A method in accordance with the invention can be implemented using the surface plasmon resonance on balls, whether in reflection or transmission. This technique is presented, for example, in the case of reflective use by Frederix & al, "*Biosensing based on light absorption on nanoscaled gold and silver nanoparticles*", Anal. Chem. 2003, vol. 75, pp. 6894-6900. The dielectric medium considered is rather a liquid, but can be used for a gaseous medium and therefore an electronic nose.

A method in accordance with the invention can also be implemented using plasmon resonance based on nanocavities. For example, Zhao Hua-Jin's article, "*High sensitivity refractive index gas sensing enhanced by surface plasmon resonance with nano-cavity anteanna array*", 2012, Chinese Physical Society and IOP Publishing Ltd, Chinese Physics B, vol. 21 (8), pp. clearly indicates that such nanocavities are sensitive to a change in local optical index. This can therefore be used to perform a calibration, for example for an electronic nose.

Moreover, the use of plasmon resonance is not the only possible technique to implement the invention.

Thus, a measurement technique based on refractometry can be considered to measure a change in the optical index. For this purpose, an optical sensor of the "optical resonator" type can be used. In this case, the resonator fulfils the function of the metal layer of a plasmon effect sensor.

Reference can be made to Luchansky & al's article "*High-Q optical sensors for chemical and biological analysis*", Analytical chemistry, 2011, vo. 84 (2), pp. 793-821.

Reference may also be made to Kim & al.'s article, "*Integrated photonic glucose biosensor using a vertically coupled microring resonator in polymers*", Optics Communications, 2008, vo. 281 (18), pp. 4644-4647 which uses this property to measure optical indices in liquid media.

Reference may also be made to Passaro et al, "Ammonia Optical Sensing by Microring Resonators", Sensors 2007, vol. 7, pp. 2741-2749 which measures local variations in optical index generated by gaseous ammonia. In particular, it is noted that the diagram on page 7744 shows that the measurement is carried out by changing the optical index. In this respect, it may therefore be sensitive to a pressure or temperature variation.

In the examples provided above, the gaseous medium of interest used to perform calibration is dry air. The invention is not limited to dry air. In particular, the gaseous medium of interest for calibration may be, but not limited to, ambient air, a carrier gas, i.e. one that may carry a gas to be measured, such as volatile organic compounds (VOCs).

In addition, in practice, the corrective factors can be obtained during the manufacture of the electronic nose but also by the user in the same environment as his measurements of interest, or during maintenance for example.

The invention claimed is:

1. A method for calibrating an electronic nose, said electronic nose comprising a plurality of optical sensors arranged on a surface and capable of being in contact with a gaseous medium of interest, said optical sensors being capable of delivering a signal representative of the local optical index of the gaseous medium of interest when they are excited by photons, the method being characterized in that it comprises the following steps, after having placed the electronic nose in a gaseous medium of interest at the initial pressure $P_0$ and the initial temperature $T_0$:
   a) emitting photons in the direction of the sensors so as to excite said sensors;
   b) measuring the signal delivered by each of the sensors, this measurement providing as many responses as there are sensors;
   c) modifying the pressure and/or temperature of the gaseous medium of interest;
   d) repeating step b); and
   e) for each sensor, determining a correction factor such that a variation in the signal between steps d) and b) corrected by the correction factor is equal or substantially equal to a variation in the signal between these same steps for a reference, said reference being provided by a reference sensor or a combination of reference sensors.

2. The method for calibrating an electronic nose according to claim 1, wherein, prior to step a), the initial pressure $P_0$ and/or the initial temperature $T_0$ of the gaseous medium of interest is determined.

3. The method for calibrating an electronic nose according to claim 1, wherein the measurement performed in step b) or d), for example a reflectivity or transmittivity measurement, is carried out over a period of between 0.1 s and 60 mn, preferably between 1 s and 10 mn, then averaged.

4. The method for calibrating an electronic nose according to claim 1, wherein, before implementing step e), steps c) and d) are repeated N times, with N a natural integer greater than or equal to 1, so that the pressure and/or temperature of the gaseous medium of interest is different from a pressure and/or temperature of the gaseous medium of interest for which a measurement has already been made.

5. The method for calibrating an electronic nose according to claim 1, wherein, in step c), the pressure and/or temperature of the gaseous medium of interest is modified to another known value.

6. The method for calibrating an electronic nose according to claim 1, wherein in step c):
   the pressure of the gaseous medium of interest is modified by a value between +10 mbar and +2 bar, preferably between +50 mbar and +150 mbar or by a value between −10 mbar and −900 mbar, preferably between −50 mbar and −150 mbar; and/or
   the temperature of the gaseous medium of interest is modified by a value between +1° C. and +100° C., preferably between +5° C. and +15° C. or between −1° C. and −50° C., preferably between −5° C. and −15° C.

7. The method for calibrating an electronic nose according to claim 5, wherein, just before step e), an additional step is implemented consisting in modifying the pressure and/or temperature of the gaseous medium of interest to the initial pressure $P_0$ and/or initial temperature $T_0$.

8. The method for calibrating an electronic nose according to claim 1, wherein the optical sensor is selected from a plasmon effect sensor, for example on a flat surface, optical fiber or nanocavities or a sensor capable of operating by refractometry, for example a resonator sensor.

9. A method for calibrating an electronic nose, said electronic nose comprising a plurality of optical sensors arranged on a surface and capable of being in contact with a gaseous medium of interest, said optical sensors being capable of delivering a signal representative of the local optical index of the gaseous medium of interest when excited by photons, the method being characterized in that it comprises the following steps, after having placed the electronic nose in a gaseous medium of interest at the initial pressure $P_0$ and the initial temperature $T_0$:
  A) determining the initial pressure $P_0$ and the initial temperature $T_0$ of the gaseous medium of interest;
  B) emitting photons in the direction of the optical sensors so as to excite said sensors;
  C) measuring the signal delivered by each of the optical sensors, this measurement providing as many responses as there are optical sensors;
  D) modifying the pressure and/or temperature of the gaseous medium of interest to another or other known values;
  E) repeating step C); and
  F) for each sensor, calculating the evolution of the optical index of the gaseous medium of interest using the measurements made in steps C) and E).

10. The method for calibrating an electronic nose according to claim 9, wherein, prior to step A), the pressure and/or temperature of the gaseous medium is adjusted to a predetermined value.

11. The method for calibrating an electronic nose according to claim 9, wherein the measurement performed in step C) or E), for example a reflectivity or transmittivity measurement, is carried out over a period of between 0.1 s and 60 mn, preferably between 1 s and 10 mn, and then averaged.

12. The method for calibrating an electronic nose according to claim 9, wherein, before implementing step F), steps D) and E) are repeated N times, with N a natural integer greater than or equal to 1, so that the pressure or, as appropriate, the temperature of the gaseous medium of interest is different from a pressure or, as appropriate, a temperature of the gaseous medium of interest for which a measurement has already been made.

13. The method for calibrating an electronic nose according to claim 9, wherein in step D):
  the pressure of the gaseous medium of interest is modified by a value between +10 mbar and +2 bar, preferably between +50 mbar and +150 mbar or by a value between −10 mbar and −900 mbar, preferably between −50 mbar and −150 mbar; and/or
  the temperature of the gaseous medium of interest is modified by a value between +1° C. and +100° C., preferably between +5° C. and +15° C., or between −1° C. and −50° C., preferably between −5° C. and −15° C.

14. The method for calibrating an electronic nose according to claim 9, wherein, just before step F), an additional step is implemented consisting in modifying the pressure and/or temperature of the gaseous medium of interest at the initial pressure $P_0$ and/or initial temperature $T_0$.

15. The method for calibrating an electronic nose according to claim 9, wherein the optical sensor is selected from a plasmon effect sensor, for example on a flat surface, optical fiber or nanocavities, or a sensor capable of operating by refractometry, for example a resonator sensor.

* * * * *